United States Patent
Myers

(10) Patent No.: US 8,263,096 B2
(45) Date of Patent: Sep. 11, 2012

(54) METHOD FOR INCORPORATING HIGH LEVELS OF EMOLLIENT OILS INTO BODYWASH

(75) Inventor: E. Gary Myers, Payson, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 13/233,334

(22) Filed: Sep. 15, 2011

(65) Prior Publication Data

US 2012/0003338 A1    Jan. 5, 2012

Related U.S. Application Data

(60) Division of application No. 12/463,974, filed on May 11, 2009, which is a continuation-in-part of application No. 11/560,982, filed on Nov. 17, 2006, now abandoned.

(60) Provisional application No. 60/597,257, filed on Nov. 18, 2005.

(51) Int. Cl.
*A61K 8/00* (2006.01)
*A61K 8/02* (2006.01)

(52) U.S. Cl. ......... 424/401; 510/130; 514/937; 514/938

(58) Field of Classification Search .................. 424/424; 510/130; 514/937, 938
See application file for complete search history.

(56) References Cited

U.S. PATENT DOCUMENTS

| 6,190,674 B1 * | 2/2001 | Beerse et al. | 424/401 |
| 2004/0235693 A1 * | 11/2004 | Wei et al. | 510/130 |

* cited by examiner

*Primary Examiner* — Gina C Yu
(74) *Attorney, Agent, or Firm* — David K. Benson

(57) ABSTRACT

Bodywash compositions incorporating high levels of emollient oils and a method for incorporating such high levels of emollient into bodywash compositions.

13 Claims, No Drawings

METHOD FOR INCORPORATING HIGH LEVELS OF EMOLLIENT OILS INTO BODYWASH

CROSS-REFERENCE TO RELATED APPLICATIONS

This application is a Divisional of U.S. patent application Ser. No. 12/463,974 filed May 11, 2009 and entitled "Composition Incorporating Emollient Oils Into Bodywash" which in turn is a continuation-in-part of U.S. patent application Ser. No. 11/560,982 filed Nov. 17, 2006 and entitled "Composition Incorporating Emollient Oils Into Bodywash" which in turn claims the benefit of U.S. Provisional Patent Application Ser. No. 60/597,257 filed Nov. 18, 2005 and entitled "Composition Incorporating Emollient Oils Into Bodywash".

FIELD OF INVENTION

The present invention is generally directed towards a bodywash composition. More particularly, the present invention is directed towards a bodywash composition incorporating high levels of emollient oils and a method for incorporating such high levels of emollient oils into a bodywash.

BACKGROUND OF THE INVENTION

Personal cleansing products have attempted to meet a variety of product characteristics desired by consumers. In general, a suitable cleansing product must exhibit good cleaning and lathering characteristics while still being mild to the skin. More beneficial are products which do not irritate the skin and leave the skin feeling moisturized.

One type of traditional moisturizing formulation includes oil and water emulsions. These formulations are created by emulsifying non-soluble skin conditioning oils into water based cleansing formulations. These formulations are balanced between the cleansing properties of the water phase and the softening effects of the oils deposited on the skin. Stability of these formulations is achieved by using an excess of surfactants present in the emulsion phase. However, emulsification of oils in water based cleansers negatively impacts the lathering and cleansing properties of the cleansers. High oil content often drastically reduces lathering ability of the product. Furthermore, surfactants, responsible for the cleansing effects, are often irritating to the skin. As such, increasing surfactant use so that more emollient oil can be incorporated into a particular composition may have no net benefit to the softening and/or cleansing characteristics of the bodywash.

Thus, there is a need to stably increase the amount of emollient oil in bodywash products without significantly impacting lather and cleansing properties while at the same time limiting skin irritation and increasing skin conditioning effects.

SUMMARY OF THE INVENTION

While the way in which the present invention address the disadvantages of the prior art will be discussed in greater detail below, in general, the present invention provides a high oil bodywash composition that effectively cleanses and softens the skin. Additionally, the present invention provides a method for incorporating high levels of emollient oil into high oil bodywash compositions thereby increasing skin conditioning effects.

In accordance with an exemplary embodiment of the present invention, the high oil bodywash composition preferably comprises a dispersion (e.g., comprised of an emollient oil, a surfactant, and water), a bodywash base, and optional additional ingredients, for example, preservatives, fragrances, color adjusters, antibacterial agents, and/or vitamins. In an exemplary embodiment, the highly stable dispersion is present in an amount preferably from about 20 to about 25 percent by weight of the high oil bodywash composition.

DETAILED DESCRIPTION

The following descriptions are of exemplary embodiments of the invention only, and are not intended to limit the scope or applicability of the invention in any way. Rather, the following description is intended to provide convenient illustrations for implementing various embodiments of the invention. As will become apparent, various changes may be made in the compositions described in these embodiments without departing from the spirit and scope of the invention.

In accordance with various aspects of the present invention, a high oil bodywash composition that effectively cleanses and softens the skin is provided. For example, in accordance with various embodiments of the invention, the high oil bodywash may be formulated so that high levels of emollient oils are delivered to the skin by vigorously rubbing the liquid product on the skin under running water. As a result, the oils are easily felt on the hands during washing without a decrease in lather volume. Upon towel drying, the oils leave the skin feeling soft and treated. While the invention will be described in this context, it should be appreciated that other uses as are now known or hereafter devised by those skilled in the art may be made of the compositions set forth herein.

In accordance with various embodiments of the present invention, the high oil bodywash composition preferably comprises a highly stable dispersion, a bodywash base, and optional additional ingredients, for example, preservatives, fragrances, color adjusters, antibacterial agents, and/or vitamins.

In accordance with one aspect, of one embodiment of the present invention, the high oil bodywash composition comprises a highly stable dispersion. As mentioned above, one type of traditional moisturizing formulation includes emulsions of oil and a bodywash base. Stability of these formulations is achieved by using an excess of surfactants present in the emulsion phase. A dispersion is a generally stable or unstable mixture of at least two immiscible substances. Providing a dispersion of emollient oil that is stable prior to mixture with a bodywash base, for example, significantly decreases the amount of surfactants necessary to stabilize the high oil bodywash composition. By so doing, this invention provides for an increased amount of emollient oil that does not noticeably impact lather, or cleansing properties, increase skin irritation, or decrease skin conditioning effects.

In general, the dispersion may be comprised of other composition ingredients during processing to deliver an effective amount of oil into the bodywash base composition. Exemplary compositions may include: one or more emollients, one or more humectants, one or more preservatives, one or more antibacterial agents, one or more fragrances, one or more surfactants, whether it be anionic, cationic, nonionic, ampholytic, amphoteric, zwitterionic surfactants, or the like, one or more antioxidants, one or more colorants, and one or more neutralizers.

The highly stable dispersion enables greater amounts of emollient oil to be incorporated into the desired bodywash base composition than without use of the highly stable dispersion. Furthermore, varying the amount of dispersion used yields varying levels of oil retained in the final high oil bodywash formulation and oil delivered to the skin. For example, in accordance with an exemplary embodiment, adding about 20 percent of the dispersion yields about 17 percent emollient oil in the final high oil bodywash formulation. In accordance with another embodiment, adding 25 percent dispersion yields about 22 percent of emollient oil in the final high oil bodywash formulation.

Without being limited to any theory, it is believed the oil becomes stabilized in the dispersion phase and initially separated from the bodywash base, but thereafter dispersed thoroughly therethrough, thereby increasing composition stability. Because of this prior stabilization in the dispersion phase and initial separation, there is increased stability in the overall high oil bodywash composition and less surfactant or other stabilizer is needed. By decreasing the amount of surfactant needed, the potential for skin irritability is decreased while maintaining cleansing effectiveness and lathering characteristics. The oil dispersion breaks down in the presence of bathing water and shear force releasing the oil to the skin. The bodywash base then provides suitable lathering characteristics.

That being said, the highly stable dispersion is preferably strong enough to survive throughout product processing but should be able to be activated by rubbing the product between the hands or other skin surfaces in the presence of water. Upon activation, the emollient oils are delivered to the skin leaving the skin feeling soft and conditioned.

As such, any composition capable of stably delivering oil into a high oil bodywash base composition may be suitable as a highly stable dispersion. For example, in accordance with various embodiments of this aspect of the present invention, the highly stable dispersion comprises an emollient oil, a surfactant, and water.

In an exemplary embodiment, the highly stable dispersion is present in an amount from about 10 to about 35 percent by weight of the high oil bodywash composition. More preferably, the dispersion is present in an amount from about 15 to about 30 percent, and most preferably, from about 20 to about 25 percent by weight of the high oil bodywash composition.

As noted above, in accordance with one embodiment of the present invention, the highly stable dispersion comprises one or more emollient oils. Emollient oils are known for moisturizing and softening the skin by depositing a layer of oil on the skin to slow water loss and increase water content. As such, any emollient may be suitable for use in the highly stable dispersion. Exemplary emollients within the spirit and scope of the invention may include, but are not limited to algae extract, borage seed oil, carrageenan extract, castor oil, corn oil, evening primrose oil, grape seed oil, jojoba oil, kukui nut oil, lecithin, macadamia oil, oat kernel meal, pea extract, pecan oil, safflower oil, sesame oil, shea butter, soybean oil, sunflower oil and/or sweet almond oil.

In accordance with various exemplary embodiments, the emollient oils are present in an amount from about 80 to about 95 percent by weight of the dispersion. More preferably, the oils are present in about 85 to about 93 percent by weight, and most preferably, the oils are present in about 88 to about 90 percent by weight of the dispersion. In accordance with these exemplary embodiments, the emollient oils comprise a combination of soybean and safflower oil present in a 50%/50% mixture. However, any single oil, combination of oils, or type of emollient now known or hereafter devised is suitable.

In accordance with an exemplary embodiment of the present invention, the dispersion comprises an effective amount of one or more surfactants. Surfactants such as anionic, cationic, nonionic, ampholytic, amphoteric, or zwitterionic surfactants, and/or mixtures thereof capable of stably dispersing oil in oil-in-water dispersions are suitable.

Specific surfactants that can be used in the dispersion include, but are not limited to, lauryl sulfates, octyl sulfates, 2-ethylhexyl sulfates, lauramine oxide, decyl sulfates, tridecyl sulfates, cocoates, lauryl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, cocamine oxide, decylamine oxide, myristamine oxide, ricinoleates, cetyl sulfates, and similar surfactants. Suitable anionic surfactants include, but are not limited to, compounds in the classes known alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxylethelyne sulfates, isethionates, or mixtures thereof.

Preferably, the surfactant is mild. That is, the surfactant provides enough cleansing benefit while not overly irritating the skin. Furthermore, an effective amount of surfactant is that which is capable of forming a highly stable dispersion of emollient oil droplets, but is activated upon rubbing with the skin in the presence of water. In a preferred embodiment, the surfactant in the dispersion is sodium laureth sulfate present in an amount from about 0.5 to about 5 percent by weight of the dispersion. More preferably, the sodium laureth sulfate surfactant is present in an amount from about 0.8 to about 2.5 percent, and most preferably, in an amount from about 1.0 to about 1.5 percent by weight of the dispersion.

In accordance with this aspect of the present invention, the highly stable dispersion further comprises water. In an exemplary embodiment, the water is present in an amount from about 5 to about 15 percent by weight of the dispersion. More preferably, the water is present from about 8 to about 12 percent, and most preferably, the water is present in about 9 to about 10 percent by weight of the dispersion.

In accordance with another aspect of the present invention, the high oil bodywash composition comprises a bodywash base. In accordance with various embodiments, the bodywash base may be of any suitable bodywash formulation now known in the art or hereafter devised. For example, a typical bodywash base comprises water, surfactants, skin feel conditioners and/or moisturizers, color and various polymers.

In accordance with an exemplary embodiment, the bodywash base is present in an amount from about 60 to about 90 percent by weight of the high oil bodywash composition. More preferably, the bodywash base is present in an amount from about 70 to about 85 percent, and most preferably, from about 75 to about 80 percent by weight of the high oil bodywash composition.

In various embodiments of the present invention, the high oil bodywash composition may optionally be configured for a variety of particular end-use purposes. Any additional ingredients may be added to the high oil bodywash composition; however, these optional ingredients should not interfere with the cleaning efficacy or the dispersion properties of the composition. For example, high oil bodywash compositions in accordance with the present invention may comprise one or more of a naturalizer, a preservative, a fragrance, a color adjuster, an antibacterial agent, and/or a vitamin, such as Vitamin E and/or Vitamin A. In accordance with various embodiments, a color slurry may be added to the high oil bodywash composition which is a dye or pigment dispersed in water or some other solvent and may contain TiO2 and a small amount of detergent to help stabilize the dispersion. Furthermore, in accordance with these embodiments, the slurry may also contain an antibacterial agent such as a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and Triclosan (i.e., 2,4,4'-trichloro-2'hydroxy-diphenylether), Triclocarban, Triclocarbanilide, or other now known or hereafter devised germicides.

Table 1 shows 2 exemplary bodywash compositions within the spirit and scope of the invention.

TABLE 1

|  |  | Exemplary Bodywash Composition #1 | Exemplary Bodywash Composition #2 |
|---|---|---|---|
|  |  | Weight percent | |
| Dispersion | 89.0% oil (50% soybean oil/50% safflower oil) 9.9% water 1.1% surfactant | 20 | 25 |
| Bodywash Base | 35-50% water 15-25% amphoteric, and or ampholytic, and or nonionic surfactant 2-8% polyethylene glycols ranging 6-12 moles of ethylene oxide 29-35% anionic surfactant 3.5-6% polyol (sorbitol, glycerin, etc.) 0.2-2.0% fragrance | 80 | 75 |
|  | Total | 100 | 100 |
|  | Oil Content in Final Bodywash Product | 17.8 | 22.25 |

In the examples described above, the bodywash is prepared using processing equipment common in this industry. Importantly the emollient oil dispersion and the bodywash base are prepared separately. The highly stable oil dispersion was prepared using a Ross Model LAB-ME vacuum mixer homogenizer at from 1000 to 2000 RPM. This Ross Homogenizer consists of a counter-rotating turbine and a high speed rotor/stator. The rotor stator head is positioned in the bottom center of the mix vessel to enable its use with very small volumes of material. During the mixing operation the outer turbine rotates clockwise and moves materials off the vessel wall and upwards. The inner blades rotate counter clockwise and move material downward and into the high speed homogenizing head. The highly stable dispersion, prepared by intensive mixing, is then added to the bodywash base with gentle mixing to prevent aeration of the total blend. The invention is not generally dependent on the bodywash base used.

In a third exemplary bodywash composition resulting in a final bodywash product with 10% oil content, the high oil bodywash produced a foam height typical of a bodywash without the high oil load. The exemplary high oil bodywash lather volume was 70 ml and the control volume was 65 ml. The lather volume was determined using the graduated cylinder method described by T. E. Woods in "Soap technology for the 1990's." The accuracy was (+/−) 5 ml.

Finally, it should be understood that various principles of the invention have been described in illustrative embodiments. However, many combinations and modifications of the above-described formulation, proportions, elements, materials and components, used in the practice of the invention, in addition to those not specifically described, may be varied and particularly adapted to specific environments and operating requirements without departing from those principles. Other variations and modifications of the present invention will be apparent to those of ordinary skill in the art, and it is the intent that such variations and modifications be covered.

What is claimed is:

1. A method of preparing a bodywash composition incorporating a high level of emollient oil comprising:
   a) preparing a stable dispersion by combining together by intensive mixing from about 80 to about 90 percent by weight of an emollient oil, from about 0.5 to about 5 percent by weight of a surfactant and from about 5 to about 15 percent by weight of water;
   b) separately preparing a bodywash base comprising about 35 to about 50 percent by weight of water, from about 15 to about 25 percent by weight of at least one surfactant selected from the group consisting of amphoteric, ampholytic and non-ionic surfactant, from about 2 to about 8 percent by weight of polyethylene glycol, from about 29 to about 35 percent by weight of an anionic surfactant, and an optional additional ingredient selected from the group consisting of: a preservative, a fragrance, a color adjustor, an antibacterial agent, and a vitamin;
   c) mixing together said stable dispersion with said bodywash base to disperse emollient oil from the stable dispersion into the bodywash base and form said bodywash composition having from about 10 to about 35 percent of said stable dispersion and from about 60 to about 90 percent by weight of said bodywash base.

2. The method of claim 1, wherein said stable dispersion is present in an amount from about 15 to about 30 percent by weight of said bodywash composition.

3. The method of claim 2, wherein said stable dispersion is present in an amount from about 20 to about 25 percent by weight of said bodywash composition.

4. The method of claim 1, wherein said emollient oil is present in an amount from about 85 to about 93 percent by weight of said dispersion.

5. The method of claim 4, wherein said emollient oil is present in an amount from about 88 to about 90 percent by weight of said dispersion.

6. The method of claim 1, wherein said emollient oil comprises a mixture of soybean oil and safflower oil present in about equal amounts.

7. The method of claim 1, wherein said surfactant is present in an amount from about 0.8 to about 2.5 percent by weight of said dispersion.

8. The method of claim 7, wherein said surfactant is present in an amount from about 1.0 to about 1.5 percent by weight of said dispersion.

9. The method of claim 1, wherein said surfactant in the stable dispersion is sodium laureth sulfate.

10. The method of claim 1, wherein water is present in an amount from about 8 to about 12 percent by weight of said dispersion.

11. The method of claim 10, wherein water is present in an amount from about 9 to about 10 percent by weight of said dispersion.

12. The method of claim 1, wherein said bodywash base is present in an amount from about 70 to about 85 percent by weight of said bodywash composition.

13. The method of claim 12, wherein said bodywash base is present in an amount from about 75 to about 80 percent by weight of said bodywash composition.

* * * * *